United States Patent [19]

Albrecht et al.

[11] 3,962,451

[45] June 8, 1976

[54] CARBAZOLE DERIVATIVES

[75] Inventors: William L. Albrecht, Cincinnati, Ohio; Robert W. Fleming, Ann Arbor, Mich.

[73] Assignee: Richardson-Merrell Inc., Wilton, Conn.

[22] Filed: June 4, 1974

[21] Appl. No.: 476,331

Related U.S. Application Data

[62] Division of Ser. No. 317,149, Dec. 21, 1972, Pat. No. 3,833,596.

[52] U.S. Cl. .............................. 424/267; 424/274; 424/248
[51] Int. Cl.² ......................................... A61K 31/445
[58] Field of Search .................. 424/248, 267, 274

[56] References Cited
UNITED STATES PATENTS

| | | | |
|---|---|---|---|
| 3,531,489 | 9/1970 | Albrecht et al. | 260/294.3 |
| 3,576,865 | 4/1971 | Fleming et al. | 260/559 |
| 3,592,819 | 7/1971 | Fleming et al. | 260/294.7 C |
| 3,647,860 | 3/1972 | Sill et al. | 260/475 FR |
| 3,720,680 | 3/1973 | Albrecht et al. | 260/293.57 |

OTHER PUBLICATIONS

Shirley, Organic Chem., Holt, Rinehart and Winston, N.Y. 1964, p. 315.

Cecil et al., A Textbook of Medicine, 9th Ed., W. B. Saunders Co., Phila., Pa., 1958, p. 1.

*Primary Examiner*—Jerome D. Goldberg
*Attorney, Agent, or Firm*—William J. Stein; Eugene O. Retter; George W. Rauchfuss, Jr.

[57] ABSTRACT

Novel 3,6-bis-basic alkanes of carbazole, their preparation and use for the prevention and inhibition of viral infections are disclosed.

7 Claims, No Drawings

CARBAZOLE DERIVATIVES

This is a division, of application Ser. No. 317,149, filed Dec. 21, 1972 now U.S. Pat. No. 3,833,596.

FIELD OF THE INVENTION

This invention relates to new organic chemical compounds, to their preparation, and to pharmaceutical compositions containing such compounds. The compounds described herein are antiviral agents which are useful in inactivating or inhibiting viruses by their administration to either an infected or a non-infected host.

BACKGROUND OF THE INVENTION

There is a growing body of information that viruses play a vital role in a broad range of diseases, some of which represent the most serious of man's ills. Arthritis, juvenile arthritis, diabetes, Hodgkin's disease and various immunological diseases and degenerative diseases of the central nervous system have been linked to viruses as the causative agents.

At present, the control of virus infections is primarily achieved by means of immunization vaccines. For example, poliomyelitis, smallpox, measles and influenza are well recognized diseases in which virus vaccines have proven effective. In general, however, virus vaccines have had only a moderate success in animal prophylaxis. Each vaccine acts primarily against a specific virus and is not heterophilic in the protection it offers. Hence, vaccines have not provided a practical solution against the wide array of infectious viruses, even when limited as for example, solely to respiratory viruses.

One approach to the control of virus-related diseases and, particularly to the spread of such virus diseases, has been to search for medicinal agents or chemotherapeutic agents which are capable of inhibiting the growth of viruses, thereby preventing the spread of disease as well as preventing further damage to cells and tissues of the animal host which have not as yet been infected. Heretofore, only a limited number of virus infections such as smallpox, Asian influenza and herpes keratitis have been prevented by chemical antiviral agents. Sulfonamides and antibiotics which have revolutionized the treatment of bacterial infections have substantially no effect upon virus infections. Certain infections caused by large viruses, such as lymphogranuloma venereum, psittacosis and trachoma have been successfully treated using antibiotics and sulfa drugs. However, the majority of infections havve not been responsive to attack by chemotherapeutic agents. Thus, it can be seen that there is a need for new chemotherapeutic agents which are effective against a broad range of virus diseases, and which at the same time, are non-toxic to the host.

As a result of a long series of investigations, applicants have discovered a novel class of 3,6-bis-basic alkane derivatives of carbazole which are particularly useful as antiviral agents. These compounds are effective against a wide spectrum of virus infections and are useful in treating such infections both prophylactically and therapeutically. To applicants' knowledge, the compounds described and claimed herein are novel compounds which have not previously been described nor reported in the literature. The instant compounds possess a wide spectrum of antiviral activity in varying degrees which could not have been predicted from a knowledge of the present state of the art.

SUMMARY OF THE INVENTION

This invention relates to new derivatives of carbazole, to their preparation and to their use as pharmaceutical agents. More particularly, the compounds of the present invention are 3,6-bis-basic alkanes of carbazole which are useful as antiviral agents. Still more particularly, the compounds of the present invention may be represented by the following general formula:

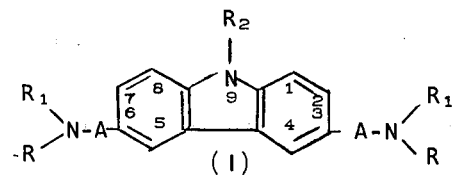

wherein A is a straight or branched alkylene chain having from 2 to 6 carbon atoms; R and $R_1$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than in the 1-position of the alkenyl group, and when R and $R_1$ are taken together with the nitrogen atom to which they are attached represent the pyrrolidinyl, morpholino or piperidino radical; $R_2$ is hydrogen or lower alkyl having from 1 to 4 carbon atoms; and their pharmaceutically acceptable acid addition salts.

The 3,6-bis-basic alkanes of carbazole of the present invention are prepared by the reduction of the corresponding 3,6-bis-basic ketones of carbazole with hydrazine in the presence of a strong base as illustrated by the following general reaction scheme:

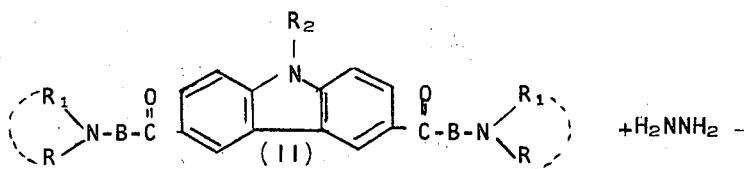

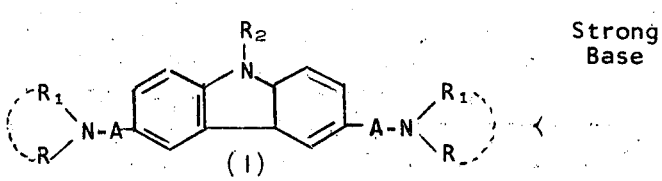

in the above reaction, the symbols A, R, $R_1$ and $R_2$ have the values previously assigned to them, and B is a straight or branched alkylene chain having from 1 to 5 carbon atoms. The 3,6-bis-basic ketones of carbazole (II) useful as starting materials in the above reaction are disclosed as preferred compounds in copending application Ser. No. 374,350, filed June 28, 1973, which is a continuation of Serial No. 57,780 filed July 23, 1970 now abandoned.

To achieve an antiviral effect the compounds of this invention are preferably administered to a host using a variety of compositions. Such compositions may be administered either prior to infection, as with a prophylactic use or treatment, or they may be therapeutically administered subsequent to infection, as with a curative use or treatment. Additionally, the compounds of this invention can be applied externally or topically directly to the virus infection, or they may be administered internally or systemically irrespective of whether the treatment is prophylactic or curative in nature. In either event, replication of the virus is inhibited or prevented with the concomitant result that the various disease sypmtoms characteristic of the pathogenic virus infection are no longer present.

DETAILED DESCRIPTION OF THE INVENTION

As can be seen from the above general formula (I), the basic alkane groups substituted on the carbazole ring consist of a basic amino function separated from the carbazole nucleus by an alkylene chain of prescribed length. It is also apparent that one of the basic alkane groups is located on each of the benzenoid portions of the carbazole ring.

The alkylene chain separating the amino function from the tricyclic ring consists of from 2 to 6 carbon atoms and represents either a straight or branched alkylene chain. Additionally, each of the alkylene groups may be the same or different; preferably, however, both groups are the same. Illustrative of the various alkylene groups which are represented by the symbol A are the: ethylene, 1,3-propylene, 1,4-butylene, 1,5-pentylene, 1,6-hexylene, 2-methyl-1,4-butylene and 3-methyl-1,5-pentylene radicals.

The basic amino function can be a primary, secondary or a tertiary amino group. preferably, each of the amino groups represented by the symbol

is a tertiary amino group. The symbols R and $R_1$ represent either hydrogen or a lower alkyl group. The term lower alkyl as used with regard to the amino groups relates to groups having from 1 to 6 carbon atoms. Illustrative of such groups can be mentioned straight or branched chain alkyl radicals such as: methyl, ethyl, 3-propyl, isopropyl, n-butyl, sec-butyl, isoamyl, n-pentyl and n-hexyl. When R and $R_1$ each represent lower alkyl, a preferred subgenus is formed.

Each R and $R_1$ of the basic amino function also represents a cycloalkyl group having from 3 to 6 carbon atoms. Such groups include the cyclopropyl, cyclobutyl, cyclopentyl and cyclohexyl radicals.

The symbols R and $R_1$ also represent an alkenyl group, having from 3 to 6 carbon atoms. In addition, the unsaturation present in this group must be in a position other than the 1-position inasmuch as any unsaturation at this point is readily hydrolyzable. Illustrative of such groups are the allyl, 3-butenyl and the 4-hexenyl radicals.

R and $R_1$ also represent various saturated, monocyclic, heterocyclic radicals when taken in conjunction with the amino nitrogen atom to which R and $R_1$ is attached. Typical of such heterocyclic groups are the pyrrolidinyl, piperidino and morpholino radicals. Compounds containing such groups are readily prepared and typify saturated, monocyclic, heterocyclic radicals which are generally useful in lieu of the dilower alkylamino groups present in the compounds of this invention.

Illustrative of specific base compounds of the present invention represented by general formula (I) are: 3,6-bis(4-dimethylaminobutyl)carbazole, 3,6-bis(5-piperidinopentyl)carbazole, 3,6-bis(4-diethylaminobutyl)-9-methylcarbazole, 3,6-bis(4-diethylaminobutyl)-9-ethylcarbazole, 9-ethyl-3,6-bis(4-piperidinobutyl)carbazole, 3,6-bis(5-dimethylaminopentyl)-9-ethylcarbazole, 3,6-bis(5-diethylamino-3-methylpentyl)-9-ethylcarbazole, 9-ethyl-3,6-bis(4-morpholinobutyl)carbazole, 9-ethyl-3,6-bis(5-pyrrolidinopentyl)carbazole, 3,6-bis(4-diallylaminobutyl)-9-ethylcarbazole, 3,6-bis(4-diethylaminobutyl)-9-propylcarbazole.

The expression "pharmaceutically acceptable acid addition salts" encompasses any non-toxic organic or inorganic acid addition salts of the base compounds represented by either formula (I) or (II). Illustrative inorganic acids which form suitable salts include hydrochloric, hydrobromic, sulfuric and phosphoric acids and acid metal salts such as sodium monohydrogen orthophosphate and potassium hydrogen sulfate. Illustrative organic acids which form suitable salts include the mono, di and tricarboxylic acids, for example, acetic, fumaric, malic, tartaric, citric, ascorbic, maleic, hydroxymaleic, benzoic, hydroxybenzoic, phenylacetic, cinnamic, salicyclic, 2-phenoxybenzoic, and sulfonic acids such as methane sulfonic acid and 1-hydroxyethane sulfonic acid. Either the mono or the di-acid salts can be formed, and such salts can exist in either a hydrated or a substantially anhydrous form.

In general, the 3,6-bis-basic alkanes of carbazole described and claimed herein are prepared by reducing the corresponding 3,6-bis-basic carbazole ketones under modified Wolff-Kishner conditions. The 3,6-bis-basic carbazole ketones are, in turn, readily prepared via a Friedel-Crafts halo-acylation of carbazole. The resulting 3,6-bis(ω-haloalkanoyl) carbazole derivatives can be aminated under a variety of conditions using either ammonia, a primary or a secondary amine. For example, the carbazole can be heated with a large excess of amine, the excess amine serving as the reaction medium and hydrohalide acceptor. Alternatively, the carbazole derivative may be heated with the amine in a suitable solvent such as toluene, dioxane or dimethylformamide to effect condensation. Specific illustrations for the preparation of 3,6-bis-basic carbazole ketones are more fully disclosed in copending application Ser. No. 374,350 filed June 28, 1973 which is a continuation of Ser. No. 57,780 filed July 23, 1970, now abandoned.

The reduction of the 3,6-bis-basic ketones of carbazole is best accomplished by heating the carbazole ketones with hydrazine in the presence of a basic catalyst. Basic catalysts which may be employed include either sodium or potassium hydroxide. Additionally, sodium-methoxide and ethoxide can be usefully employed and are equally operative in preparing the compounds of this invention.

The reduction with hydrazine proceeds through the formation of the intermediate hydrazone of the bisbasic ketone. The presence of water is to be avoided in order to prevent azine formation via the condensation of the intermediate hydrazone with the bis-basic carbonyl starting material. In order to achieve complete reduction, the reaction conducted at an elevated temperature of from about 140° to 180°C, for a period ranging from 12 to 48 hours. Conveniently, the reaction is conducted at the reflux temperature of a high-boiling solvent, such as a higher aliphatic alcohol or polyglycol. In the practice of the present invention applicants prefer to use diethylene glycol as the solvent and a reflux period of about 16 hours.

The 9-substituted lower alkyl carbazoles are obtained in almost quantitative yield by the action of a concentrated aqueous solution of sodium or potassium hydroxide upon an acetone solution of carbazole using an appropriate lower alkyl iodide or sulfate. Thus, for example, when an acetone solution of carbazole and methyl sulfate is mixed with an aqueous solution of sodium hydroxide, vigorously shaken and poured into water, an almost quantitative yield of N-methylcarbazole is obtained.

The compounds of the present invention are antiviral agents. Preferably they are administered to an animal host to prevent or inhibit viral infections. The term host refers to any viable biological material or intact animal including humans which is capable of inducing the formation of interferon and which serves as a support means for virus replication. The host can be of animal or mammalian origin. Illustratively such hosts include birds, mice, rats, guinea pigs, gerbils, ferrets, dogs, cats, cows, horses and humans. Other viable biological material such as used in the production of vaccines may also act as a host. Thus, tissue cultures prepared from organ tissues, such as mammalian kidney or lung tissue, as well as tissue cultures prepared from embryo tissue, such as obtained from amniotic cells or chick allantoic fluid, have been found to be useful hosts.

The treatment of virus infections for purposes of the present invention encompasses both the prevention and the inhibition of characteristic disease symptoms in a mammalian host susceptible to invasion by a pathogenic virus. Illustrative of mammalian virus infections which can be prevented or inhibited by the administration of the compounds of the present invention are infections caused by picornaviruses, such as encephalomyocarditis virus; myxoviruses, such as influenza $A_2$ (Jap/305) virus; arboviruses, such as Semliki forest virus; the herpes group of viruses, including herpes simplex; and the poxviruses, as for example vaccinia IHD. Thus, for example, the compounds of the present invention when administered orally or subcutaneously to mice in varying doses either shortly prior or subsequent to a fatal inoculation of a neurotropic virus such as encephalomyocarditis virus, having a $LD_{50}$ anywhere from 5 to 50, delay or prevent completely the onset of death. Salts of these compounds are generally administered in compositions containing a 0.15% aqueous hydroxyethylcellulose vehicle, whereas the free base compounds are generally administered in compositions containing a 10% aqueous surfactant vehicle in order to help solubilize the compound. In general, ten mice are used for each treated group with an additional 20 mice serving as a control group. At the time of administration the test virus is titrated in order to determine the potency or $LD_{50}$ for the particular virus pool used as a challenge. The control animals are given a placebo containing the identical volume of vehicle without, of course, the active ingredient. Because of the lethal nature of the test system employed, the anti-viral nature of the test compound is dramatically illustrated by a side by side comparison of the survival time of treated animals with the untreated control group of animals.

Respiratory viruses, such as influenza $A_2$ (Jap/305) virus, which are also lethal to the test animals employed, are administered via intranasal instillation. Animals infected in this manner have the active ingredients administered in the same manner as the test virus, and again a side by side comparison is made of the survivors of the animals treated with the untreated control animals.

Inexplicably, a mouse fatally infected with encephalomyocarditis or influenza virus occasionally survives without further treatment. This may be the result of a prior, interferon-induced infection in the mouse, or perhaps due to some genetic factor or other natural defense mechanism not presently understood. For this reason the control group selected is of sufficient size as to statistically reduce the influence of such a chance survivor upon the test results to a negligible amount.

The vaccinia test virus is typical of the dermatotrophic type viruses which respond to treatment with compositions containing the compounds of the instant invention. The vaccinia virus generally produces a nonfatal infection in mice, producing characteristic tail lesions when the virus is subcutaneously administered to the tail of the mouse. The instant compounds are administered either orally or subcutaneously either prior to or subsequent to the vaccinia infection. Tail lesions are subjectively scored on the eighth day following infection against untreated animals which serve as a control group. The compounds of the present invention have been found to be effective in varying degrees against one or all of these test viruses.

The mode of activity of the active ingredients of the present invention is not rigorously defined. Inter alia, the compounds of the present invention may induce the formation of interferon in a viable host. Interferon is a biological substance of unknown chemical structure, presumably proteinaceous in nature, which is produced by host cells in response to a viral infection. The interferon so produced acts to induce a virus inhibiting substance, which inhibits in some yet unknown manner the intracellular replication of the virus without appearing to have any inactivation effect per se upon the virus itself. A few of the viruses susceptible to interferon replication inhibition are described in Horsfall and Tamm, "Viral and Rickettsial Infections of Man," 4th Edition (1965), J.B. Lippincott Company, pp. 328-9.

As previously indicated, the compounds of the present invention may be prophylactically administered in order to prevent the spread of contagious viral diseases, or they may be therapeutically administered to a host already infected intended for their curative effect. When administered prophylactically, it is preferred that the administration be made within 0 to 96 hours prior to the infection of the host animal with a pathogenic virus. When the compounds of the present invention are administered for their curative effect, it is preferred that they are administered within about 1 or 2 days following infection of the host in order to obtain the maximum therapeutic effect.

The dosage to be administered will be dependent upon such parameters as the particular virus for which either treatment or prophylaxis is desired, the species of animal involved, its age, health, weight, the extent of infection, concurrent treatment, if any, frequency of treatment and the nature of the effect desired. A daily dose of the active ingredients will generally range from about 0.1 mg to about 500 mg per kg of body weight. Illustratively, dosage levels of the administered active ingredients for intravenous treatment range from about 0.1 mg to about 10 mg per kg of body weight; intraperitoneal administration range from about 0.1 mg to about 50 mg per kg of body weight; subcutaneous administration range from about 0.1 mg to about 250 mg per kg of body weight; oral administration may be from about 0.1 mg to about 500 mg per kg of body weight, intranasal instillation range from about 0.1 mg to about 10 mg per kg of body weight; and for aerosol inhalation therapy, the range is generally from about 0.1 mg to about 10 mg per kg of body weight.

The novel compounds described herein can also be administered in various different dosage unit forms, e.g., oral compositions such as tablets, capsules, dragees, lozenges, elixirs, emulsions, clear liquid solutions and suspensions; parenteral compositions such as intramuscular, intravenous or intradermal preparations; and topical compositions, such as lotions, creams or ointments. The amount of active ingredient contained in each dosage unit form will, of course, vary widely according to the particular dosage unit employed, the animal host being treated, and the nature of the treatment, i.e., whether prophylactic or therapeutic in nature. Thus, a particular dosage unit may contain from about 2.0 mg to over 3.0 g of active ingredient in addition to the pharmaceutical excipients contained therein.

The novel compounds described herein can be employed in conjunction or admixture with additional organic or inorganic pharmaceutical excipients. Suitable solid excipients include gelatin, lactose, starches, magnesium stearate and petrolatum. Suitable liquid excipients include water and alcohols such as ethanol, benzyl alcohol and the polyethylene alcohols either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5% to about 25% by weight, and preferably from about 1% to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil.

A preferred method of administration for the compounds of the present invention is orally either in a solid dose form such as a tablet or capsule, or in a liquid dose form such as an elixir, suspension, emulsion or syrup. Ordinarily the active ingredient comprises from about 0.5% to about 10% by weight in an oral liquid composition. In such compositions, the pharmaceutical carrier is generally aqueous in nature, as for example, aromatic water, a sugar-base syrup or a pharmaceutical mucilage. For insoluble compounds suspending agents may be added as well as agents to control viscosity, as for example, magnesium aluminum silicate or carboxymethylcellulose. Buffers, preservatives, emulsifying agents and other excipients can also be added.

For parenteral administration such as intramuscular, intravenous or subcutaneous administration, the proportion of active ingredient ranges from about 0.05% to about 20% by weight, and preferably from about 0.1% to about 10% by weight of the liquid composition. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 0.05% to about 20% by weight of the total formulation, the remaining component or components comprising excipients previously mentioned.

The active ingredients of the present invention can also be admixed directly with animal feeds or incorporated into the drinking water of animals. For most purposes, an amount of active ingredient is used which provides from about 0.0001% to about 0.1% and preferably, from about 0.001% to about 0.02% by weight of the active ingredient based upon the total weight of feed intake. The active ingredients can be admixed in animal feed concentrates, suitable for use by farmers or livestock growers for incorporation in appropriate amounts with the final animal feeds. These concentrates ordinarily comprise from about 0.5% to about 95% by weight of the active ingredient compounded with a finely divided solid carrier or flour, such as wheat, corn, soybean or cottonseed flour. Depending upon the particular animal to be fed, nutrients and fillers may also be added such as ground cereal, charcoal, fuller's earth, oyster shells and finely divided attapulgite or bentonite.

The active ingredients of the present invention can be packaged in a suitable pressurized container together with an aqueous or volatile propellant for use as an aerosol. A suitable discharge valve is fitted to an opening in the container from which the active ingredients may be conveniently dispensed in the form of a spray, liquid, ointment or foam. Additional adjuvants such as co-solvents, wetting agents and bactericides may be employed as necessary. Normally, the propellant used is a liquified gaseous compound, preferably a mixture of low molecular weight fluorinated hydrocarbons. These haloalkanes are preferred because of their compatibility with the active ingredients of the present invention, and because they are non-irritating when applied to skin surfaces. Other useful propellants include ethylene oxide, carbon dioxide, propane and nitrogen gas.

The invention described herein is more particularly illustrated by means of the following specific examples:

EXAMPLE I 3,6-Bis(4-chlorobutyryl)-9-ethylcarbazole

To a solution of 78.0 g (0.4 mole) of 9-ethylcarbazole and 141 g (1.0 mole) of 4-chlorobutyryl chloride in 1 liter of methylene chloride, which has been previously chilled to 0°C, is added portionwise 127.0 g (0.95 mole) of aluminum chloride. The mixture is stirred at room temperature for 16 hours, and the resulting complex is decomposed with a concentrated hydrochloric acid-ice mixture. The organic layer is separated, washed with water, dried over magnesium sulfate and pentane added to precipitate the desired product. Recrystallization from acetone followed by a recrystallization from an acetone methanol solution results in the formation of 3,6-bis (4-chlorobutyryl)-9-ethylcarbazole, m.p. 106°–8°C; $\lambda_{max}^{EtOH}$ 259; and $E_{1cm}^{1\%}$ 1030.

Substituting the appropriate molar equivalent of carbazole for 9-ethylcarbazole results in the formation of 3,6-bis(4-chlorobutyryl)carbazole having a m.p. 195°–8°C.

Following the same procedure but substituting an equivalent amount of 5-chlorovaleryl chloride for the 4-chlorobutyrylchloride above results in the preparation of 3,6-bis(5-chlorovaleryl)-9-ethylcarbazole.

EXAMPLE II

9-Ethyl-3,6-bis(4-piperidinobutyryl)carbazole dihydrochloride hemihydrate

A mixture of 19.5 g (0.048 mole) of 9-ethyl-3,6-bis(4-chlorobutryl)carbazole, 34.0 g (0.4 mole) of piperidine, 2.0 g of potassium iodide and 250 ml of p-dioxane is heated with stirring at the reflux temperature for a period of 68 hours and filtered while hot. Upon cooling, the mixture is diluted with 500 ml of water, and the resulting semi-solid which forms is dissolved in ether. The ether solution is washed repeatedly with water, dried over magnesium sulfate and treated with an ethereal hydrochloric acid solution resulting in the formation of 9-ethyl-3,6-bis(4-piperidinobutyryl)carbazole dihydrochloride hemihydrate, which is recrystallized from methanol-ethyl acetate solution to yield a product having a m.p. 138°–42°C; $\lambda_{max}^{EtOH}$ 258; and $E_{1cm}^{1\%}$ 699.

Following the same procedure but substituting diethylamine, dimethylamine, dibutylamine or morpholine for the piperidine above results in the preparation of 3,6-bis(4-diethylaminobutyryl)-9-ethylcarbazole dihydrochloride, 9-ethyl-3,6-bis (4-dimethylbutyryl) carbazole dihydrochloride, 9-ethyl-3,6-bis(4-dimethylaminobutyryl) carbazole dihydrochloride and 9-ethyl-3,6-bis(4-morpholinobutyryl)carbazole dihydrochloride, respectively.

EXAMPLE III

9-Ethyl-3,6-bis(4-piperidinobutyl)carbazole dihydrochloride

A solution of 10.8 g (0.019 mole) of 9-ethyl-3,6-bis(4-piperidinobutyryl)carbazole dihydrochloride hemihydrate, prepared as in Example 11, 150 ml of diethylene glycol, and 15 ml of an 85% aqueous hydrazine hydrate solution is slowly heated to 110°–20°C for a period of 2 hours with stirring. Two grams of sodium hydroxide, of a total of 10 grams (0.25 mole), is added to the mixture and heated in an open flask at 115° for 30 minutes in order to permit the escape of any water vapor present. The remaining sodium hydroxide is added in increments and the reaction mixture heated with continued stirring to a temperature of 160° for a period of 16 hours. The reaction mixture is cooled to room temperature, poured into 700 ml of an ice-water mixture, extracted with ether, and the combined ether extracts dried and acidified with hydrochloric acid. The product which precipitates is recrystallized two times from a methanol-ethyl acetate solution to yield 9-ethyl-3,6 -bis(4-piperidinobutyl) carbazole dihydrochloride having a m.p. 260°–2°C; $\lambda_{max}^{EtOH}$ 240; and $E_{1cm}^{1\%}$ 918.

EXAMPLE IV 3,6-Bis(4-piperidinobutyl)carbazole dihydrochloride

Employing the procedure of Example III but replacing 9-ethyl-3,6-bis(4-piperidinobutyryl)carbazole dihydrochloride hemihydrate with an equivalent amount of 3.6-bis(4-piperidinobutyryl)carbazole results in the preparation of 3,6-bis(4-piperidinobutyl)carbazole dihydrochloride.

EXAMPLE V 3,6-Bis(4-diethylaminobutyl)-9-ethylcarbazole dihydrochloride

A solution of 11.0 g (0.02 mole) of 3,6-bis(4-diethylaminobutryl)-9-ethylcarbazole dihydrochloride and 25 ml of an 85% aqueous hydrazine hydrate solution is dissolved in 200 ml of ethylene glycol and heated to a temperature of 165°C for a period of 18 hours. The reaction mixture is cooled and diluted with water whereupon the free base of the desired compound separates as an oil. The product is separated by decantation, washed with water, dissolved in diethyl ether and the ethereal solution dried over magnesium sulfate. The dried solution is concentrated to a small volume and placed on an aluminum oxide chromatographic column and eluted with methylene chloride. The eluate is converted to its hydrochloride salt and crystallized from a methanol-ethyl acetate solution. Recrystallization from acetone with two additional recrystallizations from a methylene chloride-acetone solution results in the preparation of 3,6-bis(4-diethylaminobutyl)-9-ethylcarbazole dihydrochloride having a m.p. 172°–4° C; and $\lambda_{max}^{EtOH}$ 240; and $E_{1cm}^{1\%}$ 907.

EXAMPLE VI

Illustration of the antiviral activity of 3,6-bis(4-diethylaminobutyl)-9-ethylcarbazole dihydrochloride Thirty mice weighing approximately 12–15 gms each are divided into two groups, a control group of 20 animals and a test group of 10 animals. All of the animals are challenged with a fatal dose ($6LD_{50}$) of encephalomyocarditis virus. The test group of animals are tested both prophylactically and therapeutically using a parenteral composition containing 3,6-bis(4-diethylaminobutyl)-9-ethylcarbazole dihydrochloride as the active ingredient dissolved in a solution of 0.15% aqueous hydroxyethylcellulose solution as the vehicle.

The composition contains the active ingredient in an amount such that each dosage contains 0.25 ml which is equivalent to a dose level of 50 mg per kg. The control group receives a subcutaneous placebo containing the same volume of vehicle without the active ingredient. Observations over a 10 day period show the termination of all the control animals within a period of from 4 to 5 days, with the treated group surviving for a statistically longer period of time.

EXAMPLE VII

Preparation of a capsule formulation

An illustrative composition for hard gelatin capsules is as follows:

| | | Per Capsule |
|---|---|---|
| (a) | 3,6-bis(4-diethylamino-butyl)-9-ethylcarbazole dihydrochloride | 200 mg |
| (b) | Talc | 35 mg |

The formulation is prepared by passing the dry powders of both (a) and (b) through a fine mesh screen and mixing them well. The powder is then filled into No. 0 hard gelatin capsiles at a net fill of 235 mg per capsule.

In the same manner, a soft gelatin capsule can be prepared in which the talc is omitted. The dry 3,6-bis(4-diethylaminobutyl)-9-ethylcarbazole dihydrochloride powder can be filled as a granulation, slug or compressed tablet directly into the rotary dye or plate mold in which the soft gelatin capsule is formed.

EXAMPLE VIII

Preparation of a tablet formulation

An illustrative composition for tablets is as follows:

| | | Per Tablet |
|---|---|---|
| (a) | 3,6-bis(4-dimethylamino-butyl)carbazole dihydrochloride | 100 mg |
| (b) | Wheat starch and granulated starch paste (10% w/v) | 15 mg |
| (c) | Lactose | 33.5 mg |
| (d) | Magnesium stearate | 1.5 mg |

The granulation obtained upon mixing lactose, starch and granulated starch paste is dried, screened and mixed with the active ingredient and magnesium stearate. The mixture is compressed into tablets weighing 150 milligrams each.

EXAMPLE IX

Preparation of an oral syrup formulation

A 2% weight per volume syrup of 3,6-bis(5-diethylamino-3-methylpentyl)-9-ethylcarbazole dihydrochloride is prepared by the usual pharmaceutical techniques in accordance with the following formula:

| | | Grams |
|---|---|---|
| (a) | Finely divided 3,6-bis(5-diethylamino-3-methylpentyl)-9-ethylcarbazole dihydrochloride | 2.0 |
| (b) | Sucrose | 33.3 |
| (c) | Chloroform | 0.25 |
| (d) | Sodium benzoate | 0.4 |
| (e) | Methyl p-hydroxybenzoate | 0.02 |
| (f) | Vanillin | 0.04 |
| (g) | Glycerol | 1.5 |
| (h) | Purified water to 100.0 ml | |

EXAMPLE X

Preparation of parenteral formulation

An illustrative composition for a parenteral injection is the following emulsion:

| Each ml Contains | Ingredients | Amount |
|---|---|---|
| 50 mg | 9-ethyl-3,6-bis(4-piperidinobutyl) carbazole dihydrochloride | 1.000 g |
| 100 mg | Polyoxyethylene sorbitan monooleate | 2.000 g |
| 0.0064 | Sodium chloride | 0.128 g |
| | Water for injection, q.s. | 20.000 ml |

The parenteral composition is prepared by dissolving 0.64 g of sodium chloride in 100 ml of water for injection, mixing the polyoxyethylene sorbitan monooleate with the 9-ethyl-3,6-bis(4-piperidinobutyl)carbazole dihydrochloride, adding a sufficient solution of the sodium chloride in water to the active ingredient and polyoxyethylene sorbitan monooleate to make 20 ml, shaking the mixture, and then autoclaving the mixture for 20 minutes at 110°C., at 15 p.s.i.g. steam pressure. The composition can be dispensed in a single ampule for multiple dosage or in 10 or 20 ampules for single dosages.

EXAMPLE XI

Preparation of dusting powder formulation

The following formulation illustrates a dusting powder for topical use:

| | | Per Kilogram |
|---|---|---|
| (a) | 9-ethyl-3,6-bis(4-piperidinobutyl)carbazole dihydrochloride | 20 gm |
| (b) | Silica aerogel | 980 gm |

The dusting powder is prepared by intimately blending the ingredients. The resulting mixture is then packaged in suitable dispensing containers.

We claim:

1. A pharmaceutical composition in dosage unit form consisting of from 2 milligrams to 3 grams of a 3,6-bis-basic alkane carbazole having the formula:

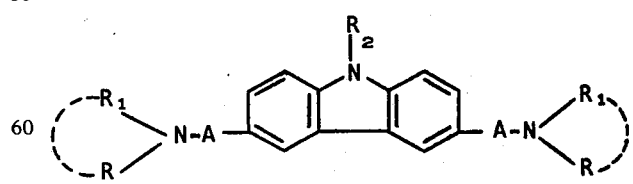

wherein A is a straight or branched alkylene chain having from 2 to 6 carbon atoms, R and $R_1$ are each selected from the group consisting of lower alkyl having from 1 to 6 carbon atoms, alkenyl having from 3 to 6 carbon atoms, in which the unsaturation is in a position other than in the 1-position of the alkenyl group, and when R and R₁ are taken together with the nitrogen atoms to which they are attached represent the pyrrolidinyl, morpholino or piperidino radical, $R_2$ is hydrogen or lower alkyl having from 1 to 4 carbon atoms, or a pharmaceutically acceptable acid addition salt thereof; and a pharmaceutical carrier.

2. A composition according to claim 1 in oral dosage unit form.

3. A composition according to claim 1 wherein each R and $R_1$ is a lower alkyl group having from 1 to 6 carbon atoms.

4. A composition according to claim 1 wherein said carbazole is 9-ethyl-3,6-bis(4-piperidinobutyl)carbazole.

5. A composition according to claim 1 wherein said carbazole is 3,6-bis(4-diethylaminobutyl)-9-ethylcarbazole.

6. A method of treating a host susceptible to invasion by pathogenic viral agents which comprises the daily prophylactic administration to said host of from 0.1 milligram to 500 milligrams per kilogram of body weight of a 3,6-bis-basic alkane carbazole having the formula

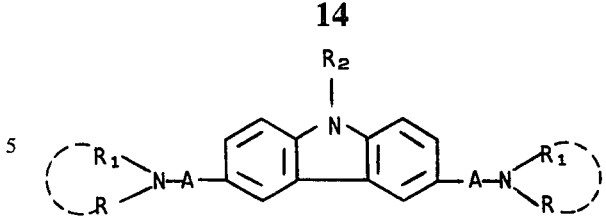

wherein A is a straight or branched alkylene chain having from 2 to 6 carbon atoms, R and $R_1$ are each selected from the group consisting of lower alkyl having from 1 to 6 carbon atoms, alkenyl having from 3 to 6 carbon atoms in which the unsaturation is in a position other than in the 1-position of the alkenyl group, and when R and $R_1$ are taken together with the nitrogen atom to which they are attached represent the pyrrolidinyl, morpholino or piperidino radical, $R_2$ is hydrogen or lower alkyl having from 1 to 4 carbon atoms or a pharmaceutically acceptable acid addition salt thereof.

7. A method of treating a host infected with a pathogenic virus which comprises administering from 0.1 milligram to 500 milligrams per kilogram of body weight per day of a carbazole of claim 6 to said host.

* * * * *